US00PP36754P2

(12) United States Plant Patent
Mowrey et al.

(10) Patent No.: US PP36,754 P2
(45) Date of Patent: Jun. 24, 2025

(54) BLUEBERRY PLANT NAMED 'DRISBLUETHIRTYONE'

(50) Latin Name: ***Vaccinium corymbosum* L.**
Varietal Denomination: DrisBlueThirtyOne

(71) Applicant: Driscoll's, Inc., Watsonville, CA (US)

(72) Inventors: Bruce D. Mowrey, Asheville, NC (US); Jennifer K. Izzo, Watsonville, CA (US); James Olmstead, Aptos, CA (US)

(73) Assignee: Driscoll's, Inc., Watsonville, CA (US)

( * ) Notice: Subject to any disclaimer, the term of this patent is extended or adjusted under 35 U.S.C. 154(b) by 0 days.

(21) Appl. No.: 18/792,258

(22) Filed: Aug. 1, 2024

(51) Int. Cl.
*A01H 5/08* (2018.01)
*A01H 6/36* (2018.01)

(52) U.S. Cl.
USPC ..... Plt./157

(58) Field of Classification Search
USPC ..... Plt./157
See application file for complete search history.

(56) References Cited

U.S. PATENT DOCUMENTS

| | | | |
|---|---|---|---|
| PP6,699 | P | 3/1989 | Wood |
| PP11,807 | P2 | 3/2001 | Lyrene |
| PP12,783 | P2 | 7/2002 | Lyrene |
| PP15,146 | P3 | 9/2004 | Hancock |
| PP19,503 | P3 | 11/2008 | Lyrene |
| PP20,436 | P2 | 10/2009 | Caster et al. |
| PP20,449 | P2 | 11/2009 | Caster et al. |
| PP20,488 | P2 | 11/2009 | Caster et al. |
| PP24,407 | P3 | 4/2014 | Caster et al. |
| PP24,489 | P3 | 5/2014 | Lyrene et al. |
| PP24,568 | P3 | 6/2014 | Caster et al. |
| PP24,569 | P3 | 6/2014 | Caster et al. |
| PP24,605 | P3 | 7/2014 | Caster et al. |
| PP26,287 | P3 | 1/2016 | Caster et al. |
| PP26,451 | P3 | 3/2016 | Rodriguez et al. |
| PP26,537 | P3 | 3/2016 | Caster et al. |
| PP26,643 | P3 | 4/2016 | Caster et al. |
| PP26,748 | P3 | 5/2016 | Rodriguez et al. |
| PP27,622 | P3 | 1/2017 | Caster et al. |
| PP28,933 | P2 | 2/2018 | Caster et al. |
| PP31,649 | P2 | 4/2020 | Caster et al. |
| PP31,650 | P2 | 4/2020 | Caster et al. |
| PP31,685 | P2 | 4/2020 | Mowrey et al. |
| PP31,698 | P2 | 4/2020 | Mowrey et al. |
| PP32,267 | P2 | 10/2020 | Caster et al. |
| PP32,744 | P3 | 1/2021 | Caster et al. |
| PP32,876 | P2 | 3/2021 | Mowrey et al. |
| PP33,066 | P2 | 5/2021 | Mowrey et al. |
| PP33,718 | P2 | 12/2021 | Caster et al. |
| PP34,067 | P2 | 3/2022 | Caster et al. |
| PP34,179 | P2 | 5/2022 | Mowrey et al. |
| PP34,316 | P2 | 6/2022 | Mowrey et al. |
| PP35,156 | P2 | 5/2023 | Mowrey et al. |
| PP35,665 | P2 | 2/2024 | Mowrey et al. |
| PP35,829 | P2 | 5/2024 | Caster et al. |
| PP35,896 | P2 * | 7/2024 | Muñoz ..... Plt./157 |

* cited by examiner

*Primary Examiner* — Susan McCormick Ewoldt
(74) *Attorney, Agent, or Firm* — Morrison & Foerster LLP

(57) ABSTRACT

A new and distinct variety of blueberry plant named 'DrisBlueThirtyOne', particularly selected for its ability to fruit on current season's growth, as well as the large size, firmness, and flavor of its fruit, is disclosed.

6 Drawing Sheets

Latin name:

Botanical classification: *Vaccinium corymbosum* L.

Varietal denomination: The varietal denomination of the claimed variety of blueberry plant is 'DrisBlueThirtyOne'.

BACKGROUND OF THE INVENTION

Blueberry plants are perennial flowering plants with indigo-colored berries from the section *Cyanococcus* within the genus *Vaccinium*. Many commercially sold species with English common names, including blueberry, are currently classified in section *Cyanococcus* of the genus *Vaccinium* and come predominantly from North America. Many North American native species of blueberries are grown commercially in the Southern Hemisphere in Australia, New Zealand, and South American nations.

*Vaccinium corymbosum*, the northern highbush blueberry, is a North American species of blueberry which has become a food crop of significant economic importance. It is native to eastern Canada and the eastern and southern United States, from Ontario east to Nova Scotia and south as far as Florida and eastern Texas. It has been naturalized in Europe, Japan, New Zealand, and the Pacific Northwest of North America. Other common names include blue huckleberry, tall huckleberry, swamp huckleberry, high blueberry, and swamp blueberry.

Blueberries are usually erect, prostrate shrubs that can vary in size from approximately four inches to approximately 13 feet in height. In the commercial production of blueberries, the smaller species are known as "lowbush blueberries", while the larger species are known as "highbush blueberries".

Blueberry bushes typically bear fruit in the middle of the growing season. However, fruiting times can be affected by local conditions such as altitude and latitude. As such, peak crop can vary from May to August in the northern hemisphere, depending upon these conditions.

Blueberries are a popular fruit that is typically consumed as fresh fruit, individually quick frozen (IQF) fruit, or in prepared foods, such as purées, juices, jellies, jams, baked goods, snack foods, and cereals.

Blueberry is an important and valuable fruit crop. Accordingly, there is a need for new varieties of blueberry plant. In particular, there is a need for improved varieties of blueberry plant that are stable, high yielding, and agronomically sound.

SUMMARY OF THE INVENTION

In order to meet these needs, the present invention is directed to an improved variety of blueberry plant. In particular, the invention relates to a new and distinct variety of blueberry plant (*Vaccinium corymbosum* L.), which has been denominated as 'DrisBlueThirtyOne'.

Blueberry plant variety 'DrisBlueThirtyOne' was selected in Santa Cruz County, California in September 2013 and originated from a controlled cross between the female parent blueberry plant 'DrisBlueSeven' (U.S. Plant Pat. No. 24,605) and the male parent blueberry plant 'DrisBlueThirteen' (U.S. Plant Pat. No. 26,451). The original seedling of the new variety was first asexually propagated via tissue culture in Santa Cruz County, California in September 2013.

'DrisBlueThirtyOne' was subsequently asexually propagated and underwent further testing in Santa Cruz County, California for four years (2016 to 2020). The present blueberry variety has been found to be stable and reproduce true to type through successive asexual propagations via tissue culture and softwood cuttings.

'DrisBlueThirtyOne' was selected for its ability to fruit on current season's growth, as well as the large size, firmness, and flavor of its fruit.

BRIEF DESCRIPTION OF THE DRAWINGS

This new blueberry plant variety is illustrated by the accompanying photographs. The colors shown are as true as can be reasonably obtained by conventional photographic procedures. The photographs are of plants that are five years old, unless otherwise specified.

DETAILED BOTANICAL DESCRIPTION

Figure 1:
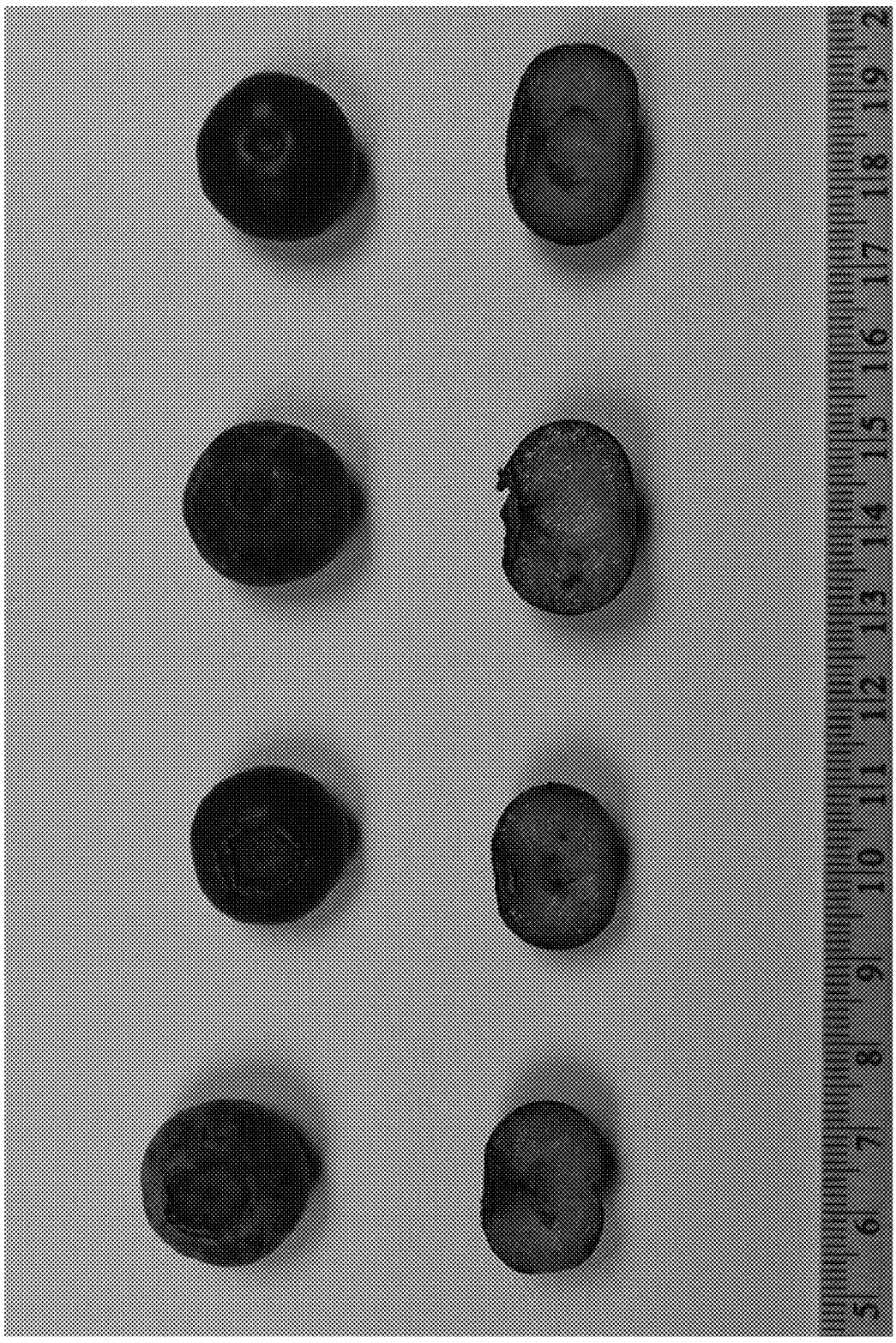
FIG. 1 illustrates whole fruit (top row) and longitudinal cross sections of fruit (bottom row) of variety 'DrisBlueThirtyOne'. Top row, from left to right: calyx side up with bloom; calyx side up without bloom; pedicel side up with bloom; and pedicel side up without bloom.
Figure 2:
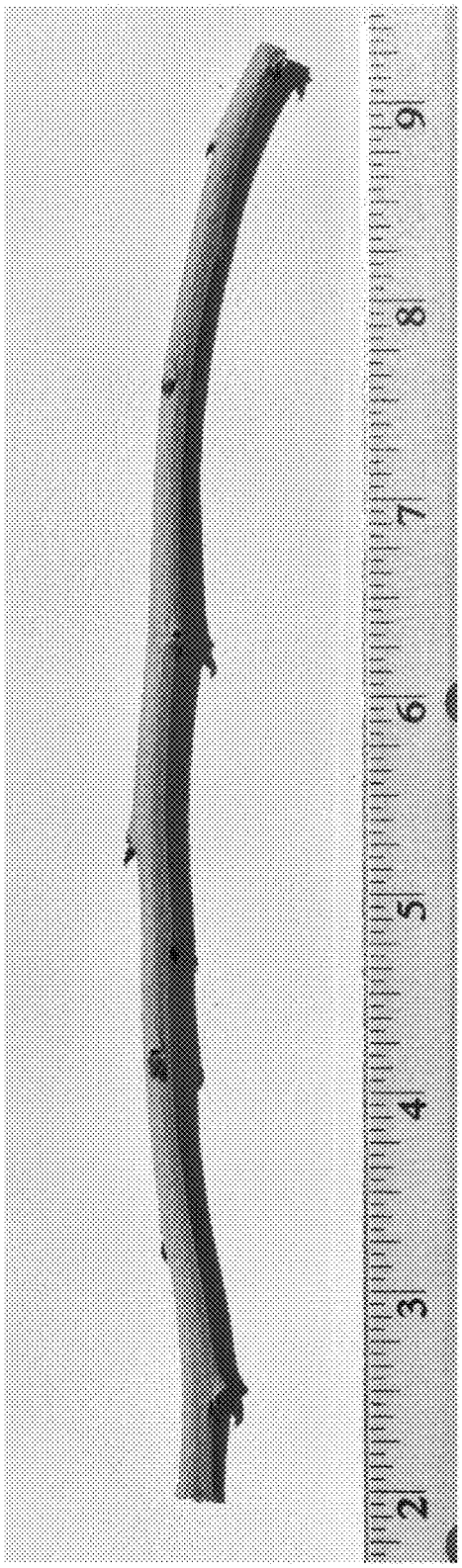
FIG. 2 illustrates a section of a cane of variety 'DrisBlueThirtyOne'.
Figure 3:
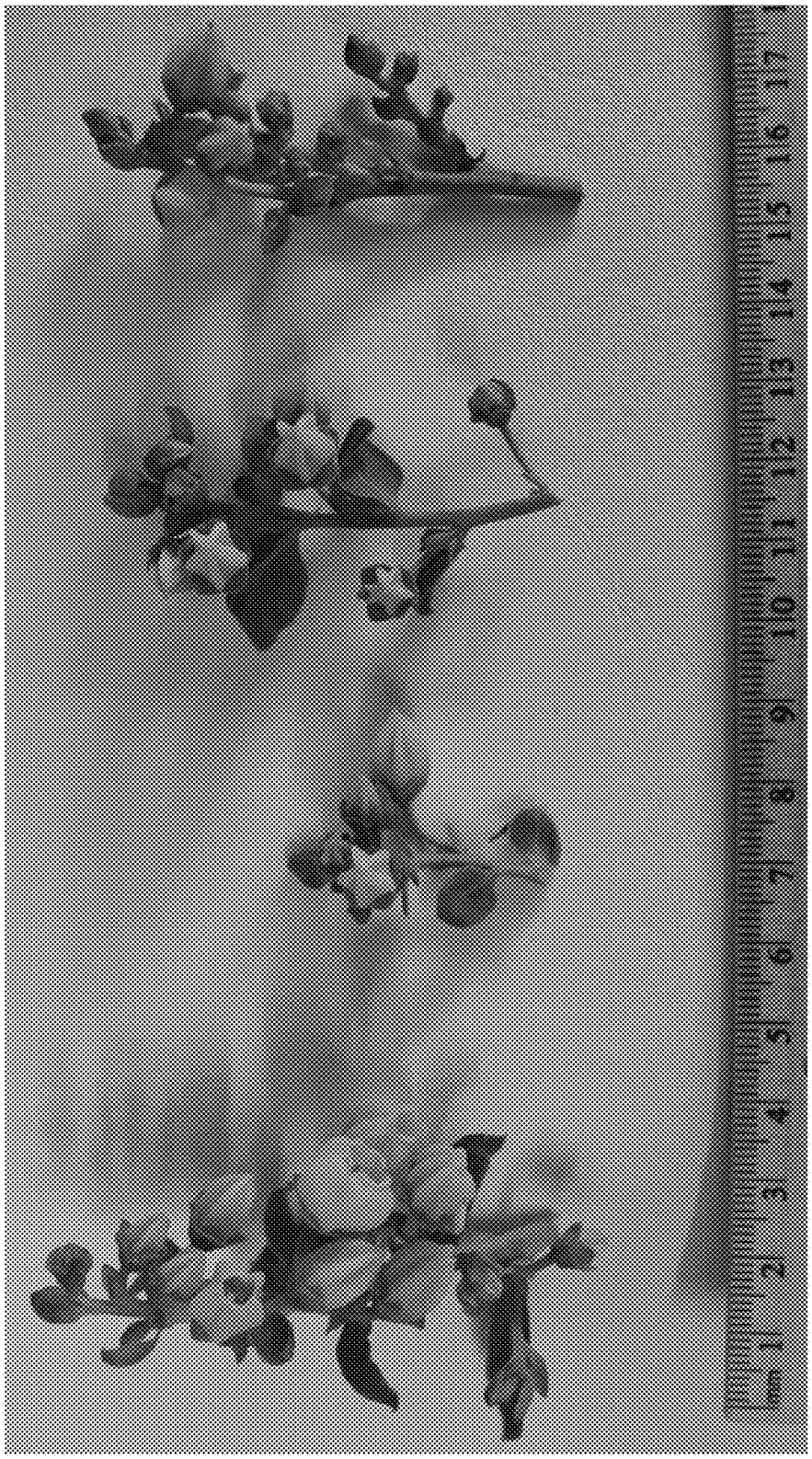
FIG. 3 illustrates clusters of flowers of variety 'DrisBlueThirtyOne'.
Figure 4:
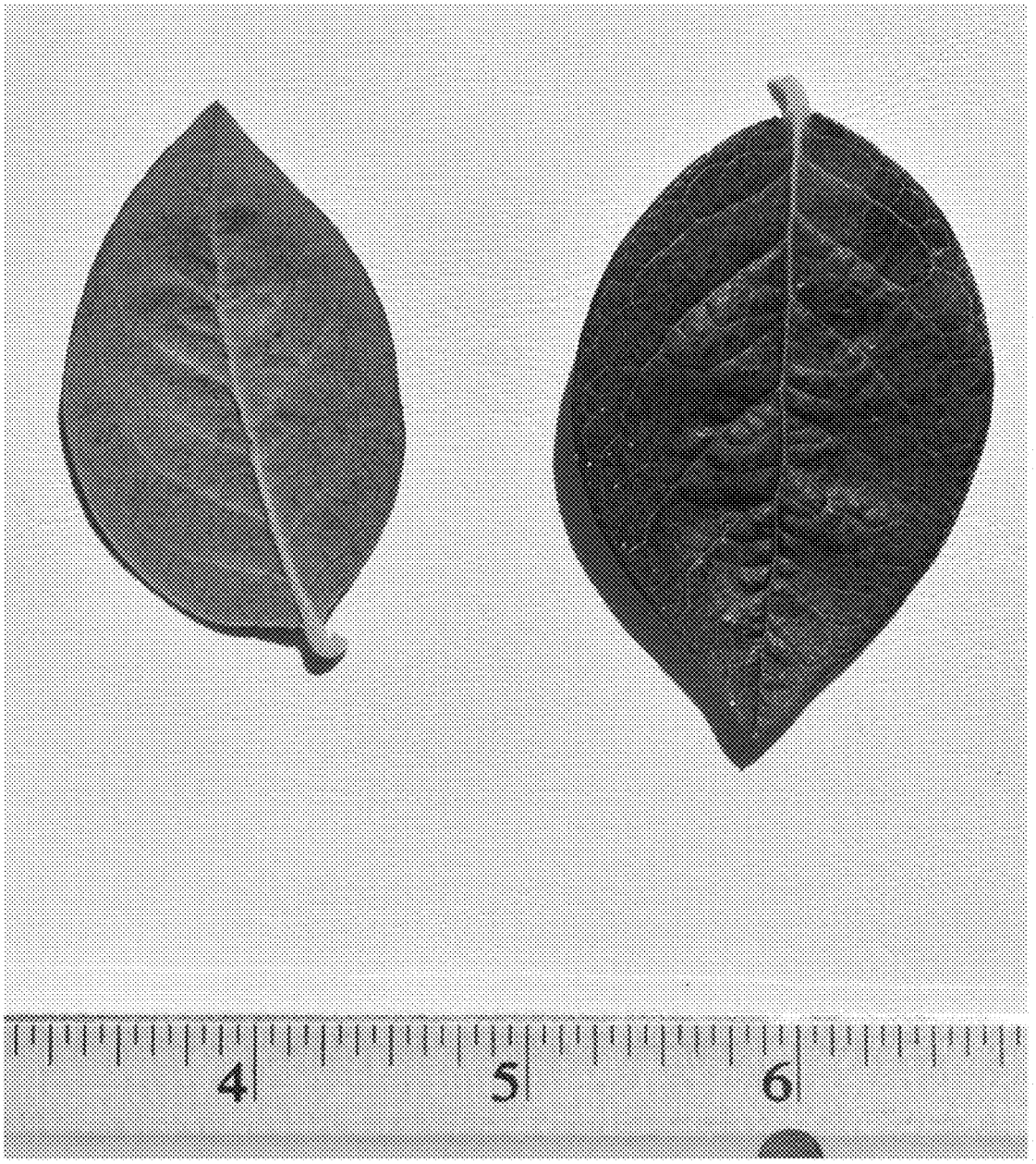
FIG. 4 illustrates the lower surface (left) and upper surface (right) of leaves of variety 'DrisBlueThirtyOne'.
Figure 5:
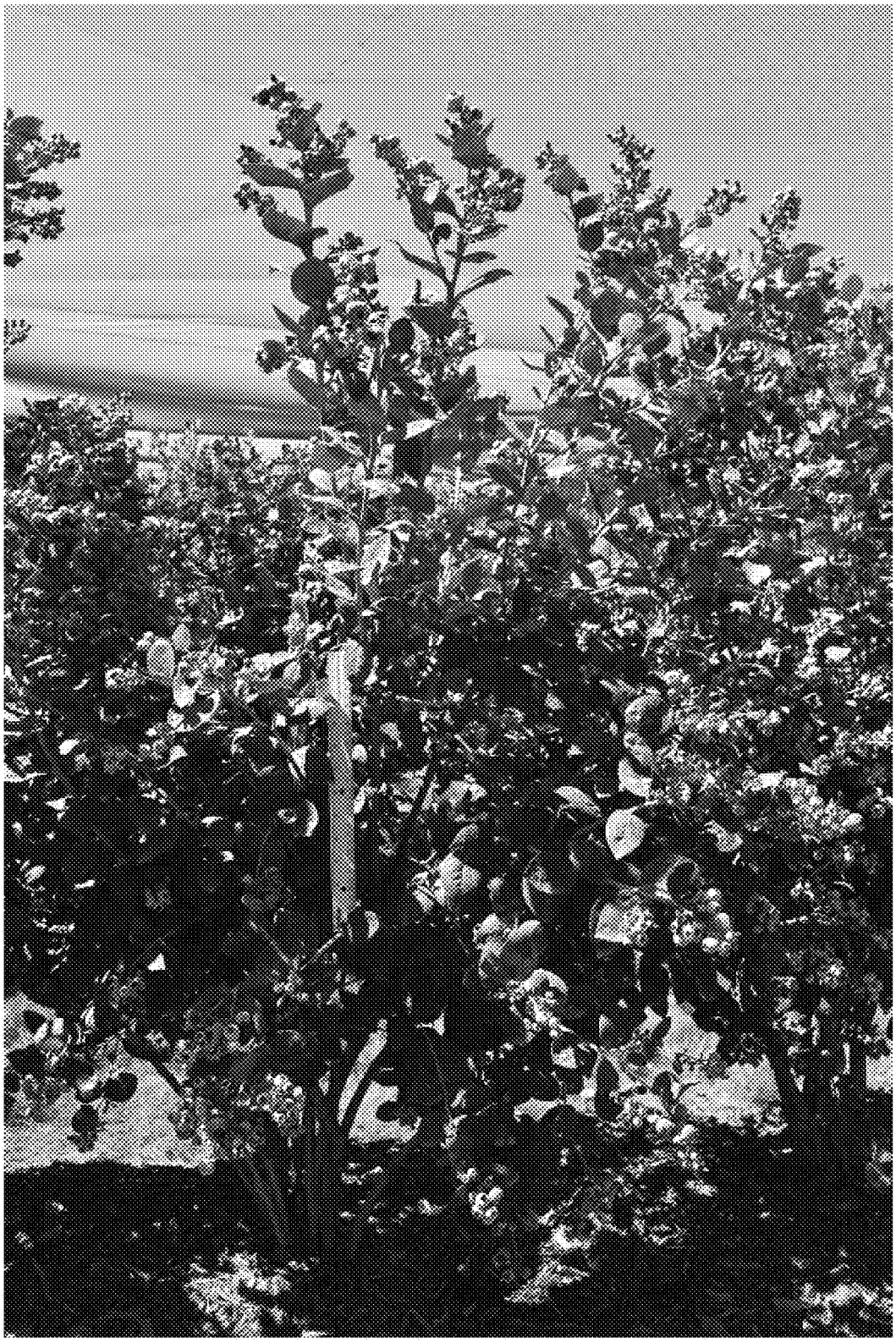
FIG. 5 illustrates a whole plant of variety 'DrisBlueThirtyOne'.
Figure 6:
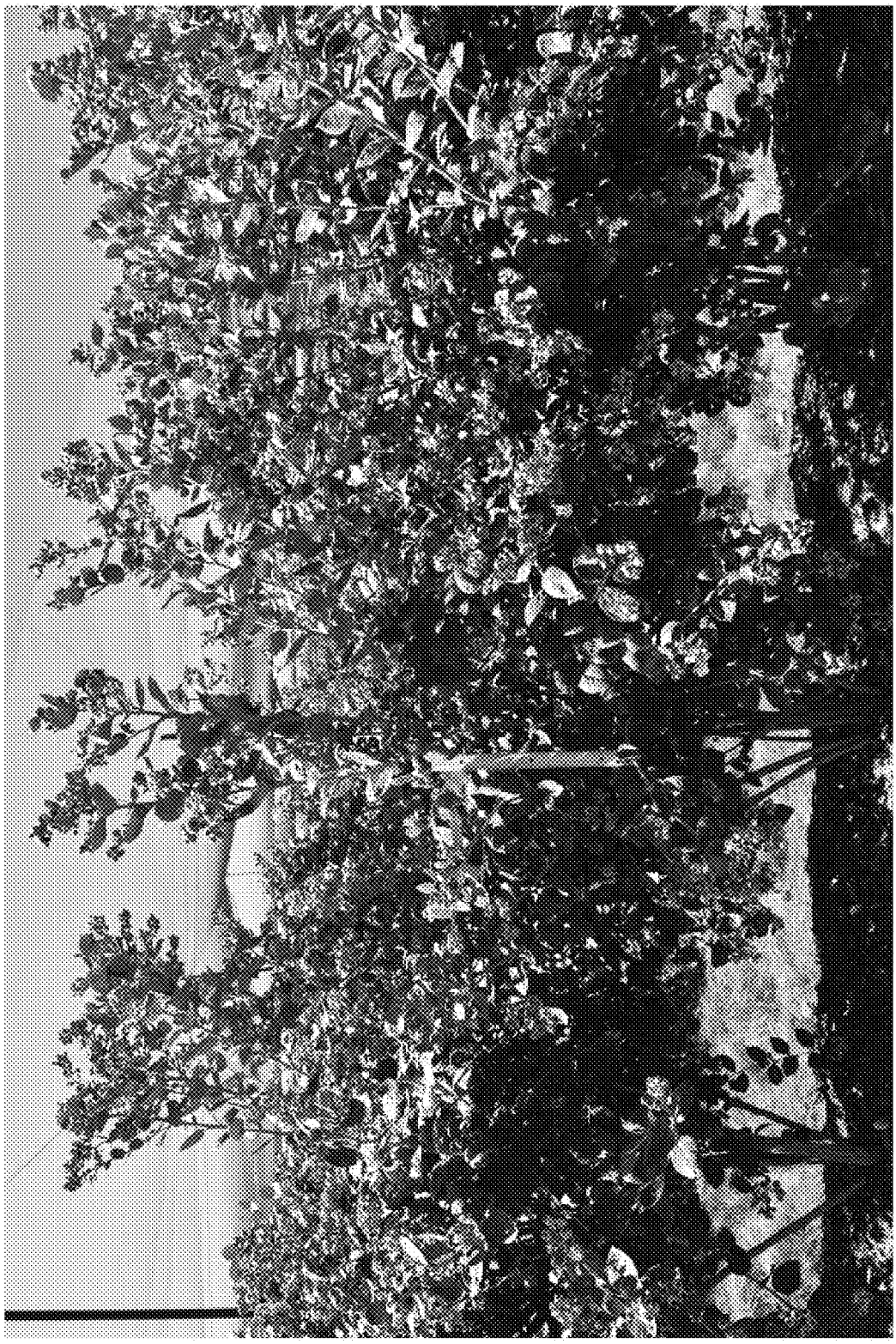
FIG. 6 illustrates another view of a whole plants of variety 'DrisBlueThirtyOne'

The following description sets forth the distinctive characteristics of 'DrisBlueThirtyOne'. The data which define these characteristics is based on observations taken in Santa Cruz County, California from 2016 to 2020. This description is in accordance with UPOV terminology. Color designations, color descriptions, and other phenotypical descriptions may deviate from the stated values and descriptions depending upon variation in environmental, seasonal, climatic and cultural conditions. 'DrisBlueThirtyOne' has not been observed under all possible environmental conditions. Unless noted otherwise, the botanical description of 'DrisBlueThirtyOne' was taken from plants that were five years old. The indicated values represent averages calculated from measurements of several plants. Color references are primarily to The R.H.S. Colour Chart of The Royal Horticultural Society of London (R.H.S.) (2015 edition). Descriptive terminology follows the *Plant Identification Terminology, An Illustrated Glossary,* 2$^{nd}$ edition by James G. Harris and Melinda Woolf Harris, unless where otherwise defined.

Classification:

*Family*.—Ericaceae.

*Botanical*.—*Vaccinium corymbosum* L.

*Common name*.—Blueberry.

*Variety name*.—'DrisBlueThirtyOne'.

Parentage:

*Female parent*.—'DrisBlueSeven' (U.S. Plant Pat. No. 24,605).

*Male parent*.—'DrisBlueThirteen' (U.S. Plant Pat. No. 26,451).

Plant:

*Growth habit*.—Upright.

*Chilling requirements*.—'DrisBlueThirtyOne' is considered to have a low chilling requirement (at least 300 hours at temperatures below 7° C. when grown in an environment that facilitates chilling conditions).

*Time of vegetative bud burst*.—When grown in Watsonville, California, and pruned in mid-January under high tunnels, vegetative bud burst occurs in February to March.

*One-year-old shoot* (*young canes*).—Internode length on the upper half: 24.1 mm. Color: RHS 145A (Yellow green).

Leaves:

*Length*.—63.75 mm.

*Width*.—43.09 mm.

*Length/width ratio*.—1.5.

*Internode length*.—24.41 mm.

*Leaf arrangement*.—Alternate.

*Shape*.—Ovate.

*Shape of base*.—Rounded.

*Shape of apex*.—Acute.

*Margin*.—Entire.

*Color on upper side*.—RHS 139A (Green).

*Glaucosity on upper side*.—Absent or weak.

*Venation pattern*.—Cross-venulate.

*Vein color*.—RHS 138D (Light yellow green).

*Texture of lower side*.—Smooth.

*Petiole*.—Length: 3.67 mm. Diameter: 1.73 mm. Color: RHS 176C (Greyish reddish orange).

Flowers:

*Flower length* (*excluding pedicel*).—12.13 mm.

*Flower width*.—8.10 mm.

*Flower length/width ratio*.—1.5.

*Flower arrangement*.—Raceme.

*Inflorescence peduncle*.—Length: 36.1 mm. Diameter: 1.8 mm.

*Flower bud*.—Length: 7.28 mm. Width: 2.60 mm. Number of flowers per bud: 3.3. Anthocyanin coloration: Medium. Anthocyanin color: RHS 185C (Moderate purplish red).

*Flower pedicel*.—Length: 11.02 mm. Diameter: 1.12 mm. Color: RHS 145A (Strong yellow green).

*Corolla*.—Shape: Urceolate. Color of corolla tube: RHS 155C (Greenish white). Anthocyanin coloration of corolla tube: Absent or very weak. Conspicuousness of ridges on corolla tube: Present and strong. Color of receptacle: RHS N138D (Brilliant green). Diameter of corolla aperture: 4.51 mm. Petal width (ridge to ridge): 5.94 mm.

*Reproductive organs*.—Style length (including stigma): 8.35 mm.

*Flowering interval on one-year-old shoot*.—March to April.

*Flowering interval on current year's shoot*.—Late June to mid-October.

Fruit:

*Length*.—12.4 mm.

*Width*.—17.6 mm.

*Length/width ratio*.—0.7.

*Weight*.—2.1 grams/fruit.

*Shape in longitudinal section*.—Oblate.

*Attitude of sepals*.—Erect to semi-erect.

*Type of sepals*.—Incurving.

*Calyx basin*.—Diameter: 7.04 mm. Depth: 3.18 mm. Diameter/depth ratio: 2.2.

*Infructescence* (*fruit cluster*).—Number of berries per cluster: 5.1. Density: Sparse. Peduncle length: 33.01 mm.

*Fruit pedicel*.—Diameter: 1.38 mm.

*Color of unripe fruit*.—RHS N144D (Yellow green).

*Intensity of bloom*.—Medium.

*Color of skin after removal of bloom on mature fruit*.—RHS 99A (Dark blue).

*Flesh color*.—RHS 193A (Pale yellow green).

*Fruit firmness*.—Very firm.

*Sweetness*.—High.

*Acidity*.—Low.

*Fruiting*.—Fruiting type: On one-year-old and current season's shoots. Harvest interval on one-year-old shoot: May to June. Harvest interval on current year's shoot: Late August to mid-December. Yield: 4.5 kg to 6.5 kg of fruit per plant from 60-month old plants when grown in Santa Cruz County, California.

Resistance to abiotic stress, pests, and diseases:

*Heat*.—Moderately susceptible.

*Spotted-wing drosophila* (*Drosophila suzukii*).—Susceptible.

*Botrytis fruit rot* (*Botrytis cinerea*).—Moderately susceptible.

COMPARISONS TO PARENTAL AND REFERENCE BLUEBERRY VARIETIES

'DrisBlueThirtyOne' differs from the female parent and reference variety 'DrisBlueSeven' (U.S. Plant Pat. No. 24,605) in that 'DrisBlueThirtyOne' has strong plant vigor, early time of beginning of flowering on one-year-old shoots, high fruit sweetness, and fruits on one-year-old and current season's shoots, whereas 'DrisBlueSeven' has medium plant vigor, very early time of beginning of flowering on one-year-old shoots, medium fruit sweetness, and fruits on one-year-old shoots only.

'DrisBlueThirtyOne' differs from the male parent and reference variety 'DrisBlueThirteen' (U.S. Plant Pat. No. 26,451) in that 'DrisBlueThirtyOne' has strong plant vigor, early time of beginning of flowering on one-year-old shoots, high fruit sweetness, and fruits on one-year-old and current season's shoots, whereas 'DrisBlueThirteen' has medium plant vigor, very early time of beginning of flowering on one-year-old shoots, medium fruit sweetness, and fruits on one-year-old shoots only.

What is claimed is:

1. A new and distinct variety of blueberry plant designated 'DrisBlueThirtyOne' as shown and described herein.

* * * * *